(12) United States Patent
Sharma et al.

(10) Patent No.: US 12,023,013 B2
(45) Date of Patent: Jul. 2, 2024

(54) BIOPSY FORCEPS WITH TISSUE PIERCING MEMBER

(71) Applicant: BOSTON SCIENTIFIC MEDICAL DEVICE LIMITED, Galway (IE)

(72) Inventors: Deepak Kumar Sharma, Muzaffarnagar (IN); Hitendra Purohit, Vadodara (IN)

(73) Assignee: Boston Scientific Medical Device Limited, Galway (IE)

( * ) Notice: Subject to any disclaimer, the term of this patent is extended or adjusted under 35 U.S.C. 154(b) by 653 days.

(21) Appl. No.: 17/247,870

(22) Filed: Dec. 28, 2020

(65) Prior Publication Data

US 2021/0236100 A1 Aug. 5, 2021

Related U.S. Application Data

(60) Provisional application No. 62/969,392, filed on Feb. 3, 2020.

(51) Int. Cl.
*A61B 10/06* (2006.01)
*A61B 1/018* (2006.01)
*A61B 10/04* (2006.01)

(52) U.S. Cl.
CPC ............. *A61B 10/06* (2013.01); *A61B 1/018* (2013.01); *A61B 10/04* (2013.01)

(58) Field of Classification Search
CPC .......... A61B 1/018; A61B 10/04; A61B 10/06
See application file for complete search history.

(56) References Cited

U.S. PATENT DOCUMENTS

| | | | |
|---|---|---|---|
| 3,895,636 A | | 6/1975 | Schmidt |
| 4,721,116 A | | 1/1988 | Schintgen et al. |
| 5,172,700 A | * | 12/1992 | Bencini ................. A61B 10/06 600/564 |
| 5,238,002 A | | 8/1993 | Devlin et al. |
| 5,373,854 A | | 12/1994 | Kolozsi |
| 5,496,317 A | | 3/1996 | Goble et al. |
| 5,535,754 A | | 7/1996 | Doherty |
| 5,715,832 A | | 2/1998 | Koblish et al. |
| 5,871,453 A | * | 2/1999 | Banik .................... A61B 10/04 600/564 |

(Continued)

*Primary Examiner* — May A Abouelela
*Assistant Examiner* — Anna Roberts
(74) *Attorney, Agent, or Firm* — Fay Kaplun & Marcin, LLP

(57) ABSTRACT

A biopsy forceps device includes a control member; a yoke coupled to the member; jaws coupled to the yoke; and a capsule. In an open configuration, the jaws are separated to receive target tissue. In a closed configuration, cutting edges of the jaws are moved toward one another to cut tissue. The capsule slidably receives the yoke and a portion of the jaws. The jaws are constrained to the closed configuration when withdrawn proximally to a first position within the capsule. When the jaws are moved to a second position, portions of the jaws are freed from the constraint capsule and spread apart. When the yoke and the jaws are moved distally and the jaws move to the open configuration, a tissue contacting structure of the yoke extends distally to engage tissue between the jaws to anchor the engaged tissue again lateral movement as the jaws contact the tissue.

13 Claims, 4 Drawing Sheets

(56) References Cited

U.S. PATENT DOCUMENTS

| | | | | |
|---|---|---|---|---|
| 6,110,127 A | * | 8/2000 | Suzuki | A61B 10/06 606/205 |
| 6,176,834 B1 | * | 1/2001 | Chu | A61B 17/3421 600/564 |
| 6,461,310 B1 | * | 10/2002 | Palmer | A61B 10/06 606/205 |
| 6,994,712 B1 | * | 2/2006 | Fisher | A61B 90/39 606/116 |
| 8,313,500 B2 | | 11/2012 | Weizman et al. | |
| 2005/0192598 A1 | | 9/2005 | Johnson et al. | |
| 2008/0147113 A1 | * | 6/2008 | Nobis | A61B 17/29 606/1 |
| 2018/0125596 A1 | * | 5/2018 | He | A61B 34/71 |

* cited by examiner

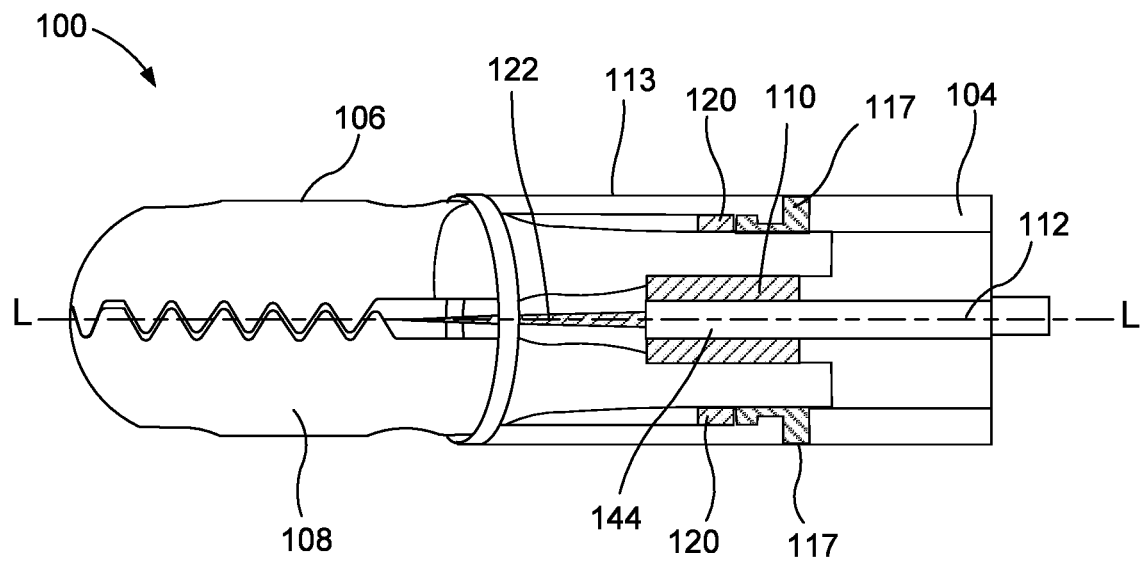
F I G. 1
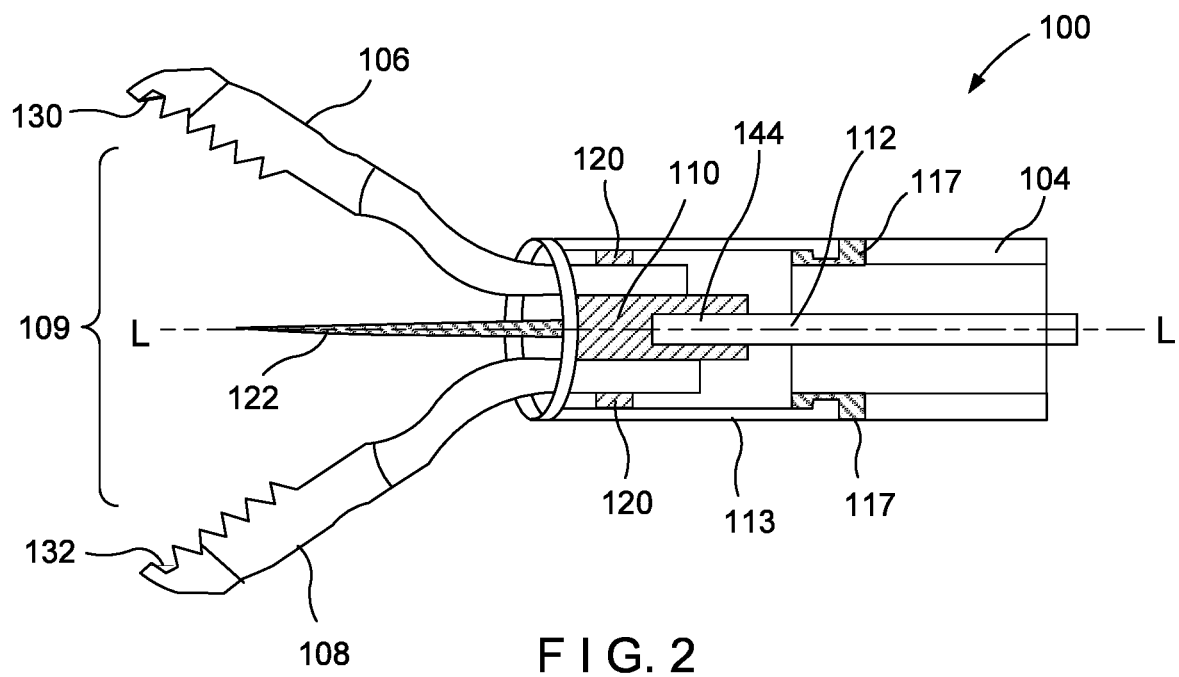
F I G. 2

BIOPSY FORCEPS WITH TISSUE PIERCING MEMBER

PRIORITY CLAIM

The disclosure claims priority to U.S. Provisional Patent Application Ser. No. 62/969,392 filed Feb. 3, 2020; the disclosure of which is incorporated herewith by reference.

FIELD

The present disclosure relates to endoscopic instruments, and more specifically, to biopsy forceps for use in endoscopic procedures.

BACKGROUND

Tissue samples are often examined to determine the presence of a pathological disorder. Endoscopic biopsy forceps may be used in conjunction with an endoscope for taking certain tissue samples from the human body for analysis. Often, the samples must be obtained from deep within the body at locations that are difficult to access by simply using forceps jaws (e.g., tissue from an area accessible via a tortuous path). In certain cases, the quality of tissue that is easily accessible may not be satisfactory for pathologists to make an accurate diagnosis. Furthermore, known forceps jaws are often difficult to maneuver for tangential bites.

SUMMARY

The present disclosure relates to a biopsy forceps device. The biopsy forceps device includes a control member extending from a proximal end to a distal end; a yoke coupled to a distal end of the control member, the yoke including a tissue contacting structure extending distally from a distal end of the yoke; and first and second jaws coupled to the yoke. The first and second jaws are biased toward an open configuration, in which the jaws are separated from one another to receive target tissue therebetween and being moveable to a closed configuration, in which cutting edges of the jaws are moved toward one another to cut a portion of the target tissue from surrounding tissue, the first and second jaws defining a tissue receiving space therebetween to house the cut tissue. The device also includes a capsule slidably receiving the yoke and a proximal portion of each of the first and second jaws. The first and second jaws are constrained to the closed configuration when withdrawn proximally to a first position within the capsule, and the first and second jaws being configured so that, when the first and second jaws are moved to a second position distal of the first position, distal portions of the jaws are freed from the constraint of the capsule and spread apart from one another under their natural bias to the open configuration, the tissue contacting structure being positioned so that, when the yoke and the first and second jaws are moved distally and the first and second jaws move to the open configuration, the tissue contacting structure extends distally to engage a portion of tissue between the first and second jaws to anchor the engaged portion of tissue against lateral movement as the first and second jaws contact the tissue adjacent to the engaged portion of tissue.

In one embodiment, the first and second jaws include concave inner surfaces defining a substantially hemispherical cup.

In one embodiment, the yoke includes radially extending protrusions that contact an inner surface of the capsule to center the yoke and the first and second jaws within the capsule.

In one embodiment, the first jaw is coupled to a first side of the yoke diametrically opposed, relative to a longitudinal axis of the capsule, to a second side of the yoke to which the second jaw is coupled.

In one embodiment, the control member is non-rotatably coupled to the yoke and the yoke and the first and second jaws are rotatably received within the capsule so that, rotation of the control wire rotates the yoke and the first and second jaws within the capsule.

In one embodiment, the device further includes a handle which, during use of the device, remains outside the body accessible to a user of the device, the handle including a first actuator operable to move the control wire proximally and distally relative to the capsule and a second actuator to rotate the control wire about the longitudinal axis of the capsule.

In one embodiment, the end effector has a length of less than 4 mm.

In one embodiment, the end effector has a length no more than 3.5 mm.

In one embodiment, the device further includes a flexible elongated member extending from a proximal end coupled to the handle to a distal end coupled to the capsule, the elongated member receiving the control member therein.

In one embodiment, the elongated member is sized to be slidably received within a working channel of an endoscope.

In one embodiment, the elongated member is coupled to the capsule via a bushing.

In one embodiment, the capsule rotates about the longitudinal axis of the capsule.

In one embodiment, the elongated member is formed as a flexible coil. In one embodiment, the tissue engage structure is formed as a tissue penetrating spike.

In one embodiment, the device further includes a plurality of protrusions at a distal end of the capsule extending radially inward toward a longitudinal axis of the capsule to prevent the first and second jaws from sliding distally out of the capsule.

The present disclosure also relates to a method for obtaining a tissue sample which includes inserting a distal portion of a biopsy forceps assembly to a target area within a living body, the distal portion including: a control member extending from a proximal end to a distal end; and an end effector including first and second jaws movable between an open configuration in which the first and second jaws are separated from one another to receive target tissue therebetween, and a closed configuration, in which cutting edges of the first and second jaws are moved toward one another to cut the target tissue away from surrounding tissue, the first and second jaws defining a tissue receiving space therebetween to house the cut tissue; moving the control member distally relative to the first and second jaws to move a yoke coupled between the control member and the first and second jaws distally so that a distal projection of the yoke member contacts the target tissue, the yoke being coupled to the first and second jaws so that distal movement of the yoke moves the first and second jaws to the open configuration; and moving the control member proximally relative to the first and second jaws to move the jaws to the closed configuration so that the cutting edges of the first and second jaws sever the target portion of tissue from the surrounding tissue.

In one embodiment, the method further includes inserting the biopsy forceps assembly through the working channel of an endoscope.

In one embodiment, the yoke and the first and second jaws are slidably received within a capsule and wherein the yoke includes a plurality of radial projections sized to slidably engage an inner surface of the capsule to maintain the yoke and the first and second jaws centered within the capsule.

In one embodiment, the device further includes a handle which, during use of the device, remains outside the body accessible to a user of the device, the handle including a first actuator operable to move the control member proximally and distally relative to the capsule and a second actuator to rotate the control member about the longitudinal axis of the capsule.

In one embodiment, the method further includes rotating the second actuator in a first direction to rotate the distal portion of the biopsy forceps assembly about the longitudinal axis of the capsule relative to the handle.

BRIEF DESCRIPTION

FIG. 1 shows a partially cross-sectional view of an end effector of a forceps device according to an exemplary embodiment of the present disclosure in a closed configuration;

FIG. 2 shows a partially cross-sectional view of the end effector of FIG. 1 in an open configuration;

DETAILED DESCRIPTION

Figure 3:
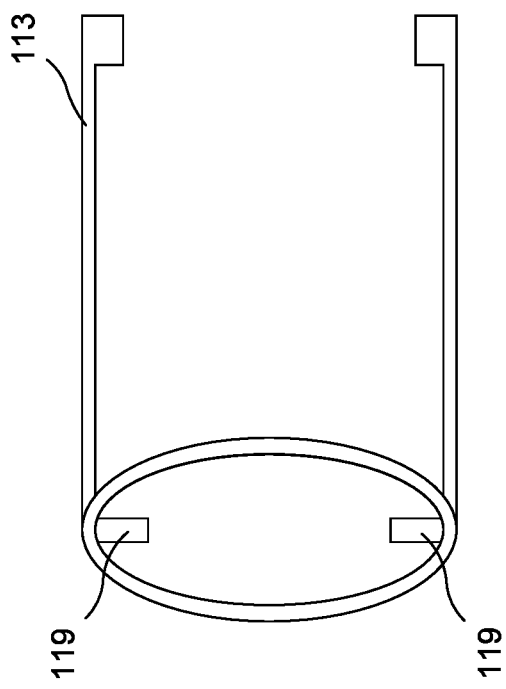
FIG. 3 shows a perspective, partially transparent view of a capsule of the end effector of FIG. 1.

The present disclosure incorporates by reference the entire disclosure of the co-pending application entitled "Biopsy Forceps with Cam Mechanism", U.S. patent application Ser. No. 16/253,951 filed on Jan. 22, 2019. The present disclosure may be further understood with reference to the following description and the appended drawings, wherein like elements are referred to with the same reference numerals. The present disclosure relates to an endoscopic forceps assembly for severing and retaining tissue samples. Exemplary embodiments of the present disclosure describe a forceps assembly that can be advanced through a working channel of a flexible endoscope, including, for example, a SpyScope™, or any other endoscopic device specifically designed and/or sized for use with the forceps assembly, and into a tissue tract. Current embodiments also include a more compact forceps design for increasing the passability and maneuverability of the forceps assembly through tight curvatures within the working channels of the endoscopic devices as well as along tortuous paths through, for example, the lumens of organs within a living body. It should be noted that the terms "proximal" and "distal," as used herein, are intended to refer to toward (proximal) and away from (distal) a user of the device.

As shown in FIGS. 1-4 and 7, a forceps assembly 10 according to an exemplary embodiment of the present disclosure includes a distal end effector 100, a proximal actuator assembly 102, and an elongate member 104 connecting the end effector 100 to the proximal actuator assembly 102. The end effector 100, as shown in FIG. 2, includes first and second jaws 106, 108, respectively, and a yoke 110 that are slidably received within a capsule 113. The yoke 110 is coupled to the first and second jaws 106, 108 and also receives and is coupled to a core wire 112. A proximal end of the capsule 113 is coupled to the elongated member 104 via a bushing 117.

Figure 4:
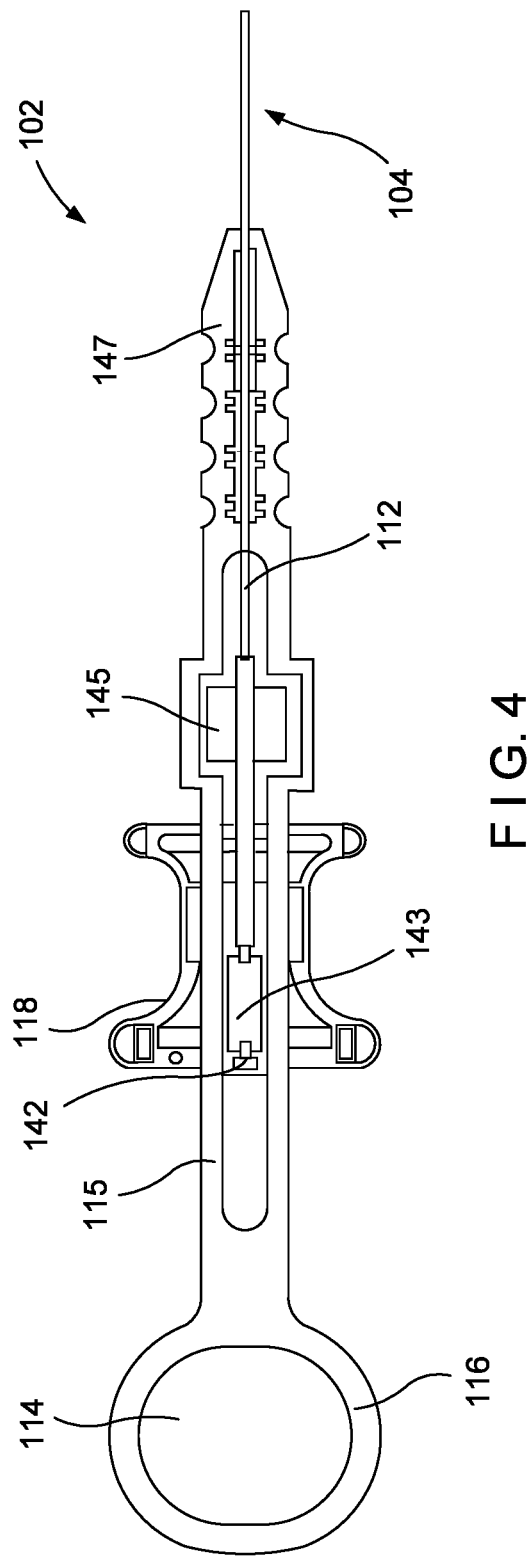
FIG. 4 shows a partially cross-sectional view of a handle assembly of the forceps device for use in conjunction with the end effector of FIG. 1.

The proximal actuator assembly 102, as shown in FIG. 4, includes a handle 114 including a proximal thumb ring 116, and a spool 118 that slides relative to the handle 114 over a longitudinal slotted member 115. The elongate member 104, in the present embodiment, is formed as a flexible coiled member and houses therein the control wire 112 that extends from the proximal actuator assembly 102 to the end effector 100. The control wire 112 is coupled to the spool 118 and the elongated member 104 is coupled to a distal end of the longitudinal slotted member 115 so that, as the spool 118 is moved proximally and distally over the longitudinal slotted member 115, the control wire 112 moves proximally and distally within the elongated member 104.

As indicated above, the yoke 110 is coupled to the control wire 112 and to the jaws 106, 108 while the capsule is coupled to the elongated member 104 via the bushing 117. Thus, as the control wire 112 is moved proximally and distally through the elongated member 104 via movement of the spool 118 over the longitudinal slotted member 115, the yoke 110 and the jaws 106, 108 are moved proximally and distally through the capsule 113. The jaws 106, 108 are formed so that they are biased toward an open, tissue receiving configuration. Thus, as the jaws 106, 108 are moved distally to extend out of the capsule 113, the jaws 106, 108 spread apart from one another so that target tissue may be received therebetween.

As the jaws 106, 108 are drawn proximally back into the capsule 113, radially outer surfaces of the jaws 106, 108 contact the wall of the capsule 113 and are forced back toward a tissue gripping configuration. As will be described below, in the tissue gripping configuration, the jaws 106, 108 are drawn together to grip, sever and retain tissue received therebetween. In order to facilitate a wide range of applications and reach targeted anatomical regions of small cross-section, the elongated biopsy forceps assembly 10 may be formed to a length of between 270 cm and 300 cm, and more preferably between 270 cm and 290 cm.

As can be seen in FIGS. 1 and 2, the yoke 110 includes two radially projecting portions 120 that extend radially outward from the yoke 110 to engage the inner surface of the capsule 113. The projecting portions 120 keep the yoke 110 and the jaws 106, 108 centered within the capsule 113 as the yoke 110 and the jaws 106, 108 are moved proximally and distally within the capsule 113. The capsule 113 has two protrusions 119 at the distal end that prevent the jaws 106, 108 from sliding distally out of the capsule 113. The protrusions 119 are sized and shaped to meet the projecting portions 120 as the jaws 106, 108 and the yoke 110 move distally out of the distal end of the capsule 113.

The yoke 110 also includes a tissue penetrating spike 122 projecting distally therefrom. The spike 122 of this embodiment extends substantially along a longitudinal axis L of the capsule 113 so that the spike 122 remains substantially centered between the jaws 106, 108 as the jaws 106, 108 are moved between the open and tissue gripping configurations. Because the jaws 106, 108 are opened through their own natural bias and no linkage (e.g., a four bar linkage) is required to connect the jaws 106, 108 to the control wire 112, the spike 122 may pass directly along the longitudinal axis L without interfering with the action of the jaws 106, 108.

FIG. 2 depicts the end effector 100 with the first and second jaws 106, 108 in the open, tissue-receiving configuration. The first and second jaws 106, 108 of this embodiment are generally cup-shaped with convex outer surfaces and concave inner surfaces such that, in the closed configuration, an inner tissue-receiving space 109 is formed between the first and second jaws 106, 108. The outer perimeter edges of the first and second jaws 106, 108 are formed as tissue cutting edges 130, 132 configured to mate with one another when in the closed configuration. For example, in this embodiment, the perimeters of the first and second jaws 106, 108 include complimentary serrated edges or teeth such that peaks of the serrations of the first jaw 106 fit within the valleys of the serrations of the second jaw 108, and vice versa. In another embodiment, the distal cutting edges 130, 132 may be straight cutting edges.

The control wire 112, as shown in FIG. 4, extends from a proximal end 142 coupled to the spool 118 via a sleeve 143 coupled thereto to a distal end 144 coupled to the yoke 110. In this embodiment, the sleeve 143 is a hypotube crimped over the control wire 112. The sleeve 143 is coupled to a rotation knob 145 received within the longitudinal slotted member 115 distally of the spool 118 so that, as the rotation knob 145 is rotated about the longitudinal slotted member 115, the control wire 112 rotates relative to the handle 114. The sleeve 143 is rotatably coupled to the spool 118 so that, as the control wire 112 is rotated via the rotation knob 145, the spool remains in position without rotating. In addition, as seen in FIG. 4, the proximal end of the elongated member 104 is coupled to the distal end of the handle 114 via a retainer 147.

Figure 5:
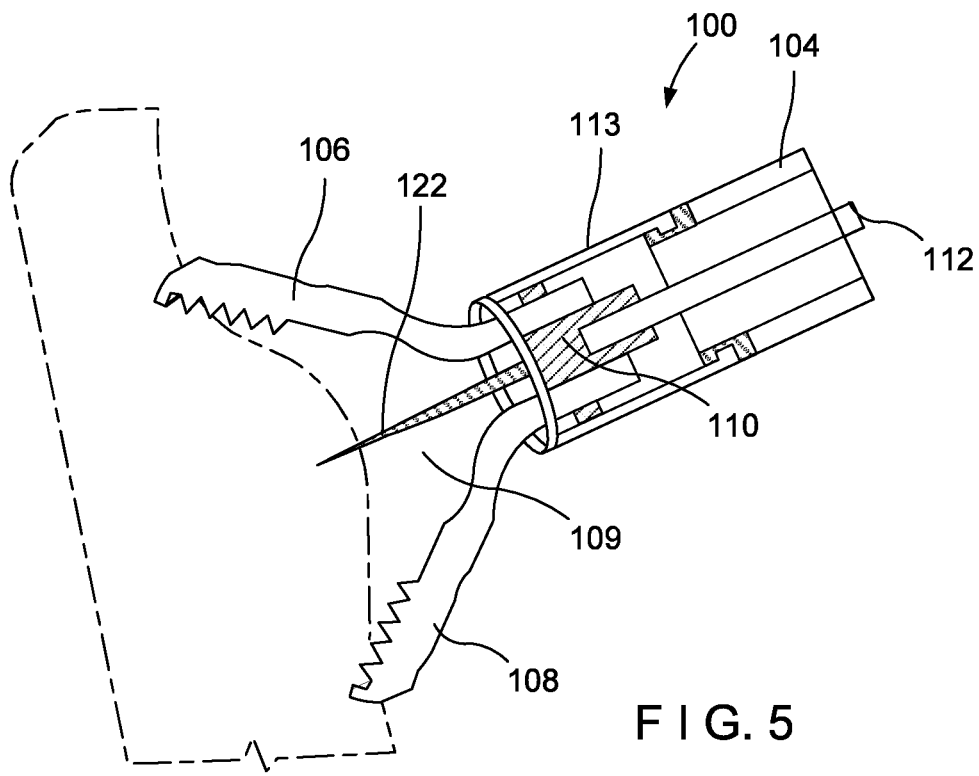
FIG. 5 shows a partially cross-sectional view of the end effector of FIG. 1 in the open configuration adjacent to target.
Figure 6:
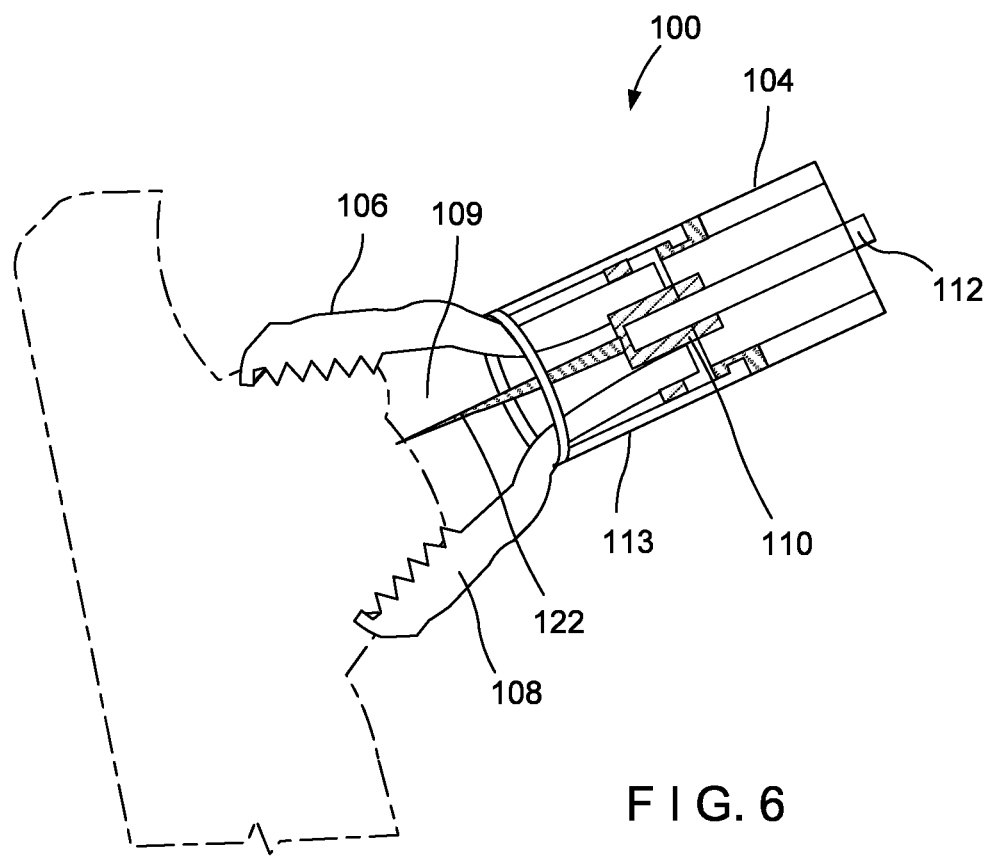
FIG. 6 shows a partially cross-sectional view of the end effector of FIG. 1 gripping the target tissue.
Figure 7:
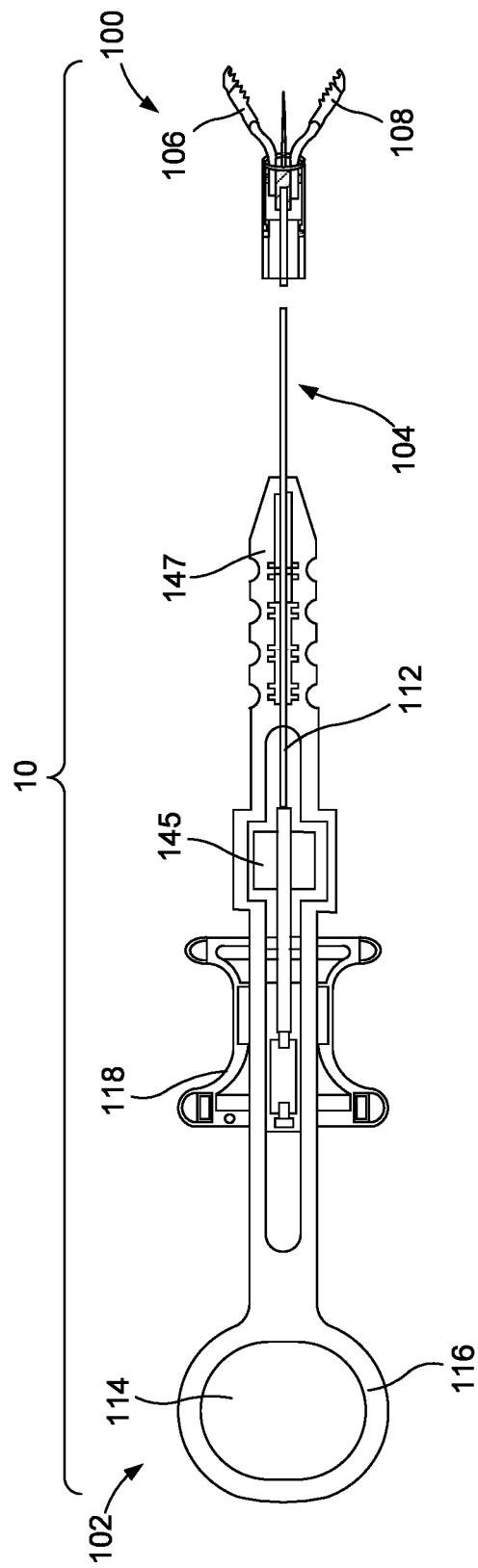
FIG. 7 shows a partially cross-sectional view of the forceps device of FIG. 1.

The spike 122 aids in maintaining a target portion of tissue in a desired position relative to the jaws 106, 108 as the target portion of tissue is captured within the end effector 100. Specifically, as shown in FIGS. 5 and 6, when the jaws 106, 108 are extended distally from the capsule and move to the open, tissue receiving configuration, the spike 122 is exposed centered between the now separated jaws 106, 108. As the end effector 100 is advanced distally toward the target tissue, the spike 122 penetrates the target tissue so that, as the jaws 106, 108 are drawn toward one another, engagement between the tissue on either or both sides of the spike 122 by the first jaw 106 and/or the second jaw 108 does not draw the target tissue off center possibly including non-targeted tissue in the sample obtained or in moving some of the targeted tissue out of center so that some of this target tissue is not included in the portion that will be gripped and severed by the jaws 106, 108.

By maintaining the tissue toward which the user has directly aimed the end effector centered between the jaws 106, 108, the spike 122 ensures that the amount of targeted tissue included in the sample is maximized. Those skilled in the art will understand that other types of tissue centering structures may be used. For example, the spike 122 may be replaced by a projecting structure that is designed to engage the target tissue and otherwise maintain the target tissue centered between the jaws 106, 108, terminating in a small flat square shape, an adhesive structure, a roughened surface, etc. so long as the structure resists lateral forces exerted, for example, by the jaws 106, 108 against the adjacent tissue.

In an exemplary embodiment, the end effector 100 has a reduced length rigid portion that enables the forceps assembly 10 of this embodiment to more easily traverse tortuous paths around tight turning radii. For example, by eliminating the linkages associated with certain end effectors the end effector 100 of this embodiment may have a rigid portion of, for example, 3.5 mm. The shortening of these components and, thus, the end effector 100, allows the end effector 100 to more easily pass through acute curvatures within a living body. Furthermore, the reduced rigid length of the end effector 100, in combination with the spike 122, reduces the number of bites required to grab a desired amount of target tissue. This reduction in the number of bites required to grab the desired amount of target tissue reduces the number of insertions of the end effector 100 into the tissue, reducing trauma to the surrounding tissue.

Turning back to FIG. 1, the elongate member 104 is coupled to, and extends proximally from, the bushing 117. The elongate member 104 and the bushing 117 may be coupled to one another via any of a variety of methods including, but not limited to, welding, soldering, adhesives, etc. In an exemplary embodiment, the elongate member 104 may be formed of a flexible, closely wound, stainless steel helical coil and may further include a thin covering or coating, such as a layer of polytetrafluroethelene (PTFE) as would be understood by those skilled in the art. The flexible coil 104 may have, for example, a circular, rectangular, or other cross-section. As one skilled in the art would understand, other shapes for the cross-section may be selected depending on the particular application. The PTFE reduces friction between the working channel of the endoscope and the elongate member 104 so that the forceps assembly 10 slides more easily within the endoscope.

In use, the forceps assembly 10 is maintained in the closed configuration and inserted into the body, e.g., through the working channel of an insertion instrument such as the endoscope which may be, for example, a SpyScope™ DS Access & Delivery Catheter. For example, an endoscope may be inserted into the duodenum to retrieve a tissue sample from the biliary tract. This often requires the deployment of the end effector 100 at an acute angle relative to a longitudinal axis of the duodenum due to the complex anatomy and location of the biliary tract. The reduced rigid length of the end effector 100 facilitates passage of the forceps assembly 10 through these tight curves, enhancing maneuverability and positioning at a desired location. The elongated member 104 along with the end effector 100 is passed through the endoscope along the tortuous path to enter a common bile duct. Once the distal end effector 100 has been positioned as desired adjacent to the target tissue, the spool 118 is advanced distally over the handle 114, moving the control wire 112 and the yoke 110 distally. This distal movement of the yoke 110 moves the jaws 106, 108 distally to extend out of the capsule 113.

As the jaws 106, 108 move distally out of the capsule 113, the natural bias of these jaws 106, 108 moves them apart from one another into the open, tissue receiving configuration. As the jaws 106, 108 open and the control wire 112 advances forward, the spike 122 pierces the target tissue, preventing this tissue from being moved laterally off center which helps to increase the depth to which an obtained sample of the target tissue may extend as seen in FIGS. 5 and 6. The first and second jaws 106, 108 are then closed by withdrawing the control wire 112 proximally, drawing the yoke 110 and the first and second jaws 106, 108 proximally until contact between the jaws 106, 108 and the capsule draws the jaws toward one another to grip and sever the target tissue.

As the first and second jaws 106, 108 close, the cutting edges along the profile of the first and second jaws 106, 108 sever the tissue captured in the tissue receiving space 109 of the first and second jaws 106, 108 from the surrounding tissue and this severed tissue sample is retained between the closed jaws 106, 108. Once the tissue has been collected within the tissue receiving space 109 between the first and second jaws 106, 108, the forceps assembly 10 is retracted proximally from the endoscope and the tissue is retrieved from the first and second jaws 106, 108 for diagnosis. If more tissue is preferred for the diagnosis, the forceps assembly 10 may be re-inserted through the endoscope for further tissue extraction in the same manner.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this disclosure is not limited to the particular embodiment disclosed, but rather modifications are also covered within the scope of the present disclosure as defined by the appended claims.

What is claimed is:

1. A biopsy forceps device, comprising:
a control member extending from a proximal end to a distal end;
a yoke coupled to a distal end of the control member, the yoke including a tissue contacting structure extending distally from a distal end of the yoke, wherein the tissue contacting structure is formed as a tissue penetrating spike;
first and second jaws coupled to the yoke, the first and second jaws being biased toward an open configuration, in which the first and second jaws are separated from one another to receive target tissue therebetween and being moveable to a closed configuration, in which cutting edges of the first and second jaws are moved toward one another to cut a portion of the target tissue from surrounding tissue, the first and second jaws defining a tissue receiving space therebetween to house the cut tissue; and
a capsule slidably receiving the yoke and a proximal portion of each of the first and second jaws, the first and second jaws being constrained to the closed configuration when withdrawn proximally to a first position within the capsule, and the first and second jaws being configured so that, when the first and second jaws are moved to a second position distal of the first position, distal portions of the first and second jaws are freed from the constraint of the capsule and spread apart from one another under their natural bias to the open configuration, the tissue contacting structure being positioned so that, when the yoke and the first and second jaws are moved distally and the first and second jaws move to the open configuration, the tissue contacting structure extends distally to engage a portion of tissue between the first and second jaws to anchor the engaged portion of tissue against lateral movement as the first and second jaws contact the tissue adjacent to the engaged portion of tissue,
wherein the yoke includes radially projecting portions that contact an inner surface of the capsule to center the yoke and the first and second jaws within the capsule, and
wherein the capsule includes a plurality of protrusions at a distal end of the capsule extending radially inward toward a longitudinal axis of the capsule to prevent the first and second jaws from sliding distally out of the capsule.

2. The device of claim 1, wherein the first and second jaws include concave inner surfaces defining a hemispherical cup.

3. The device of claim 1, wherein the first jaw is coupled to a first side of the yoke diametrically opposed, relative to a longitudinal axis of the capsule, to a second side of the yoke to which the second jaw is coupled.

4. The device of claim 3, wherein the control member is non-rotatably coupled to the yoke and the yoke and the first and second jaws are rotatably received within the capsule so that, rotation of the control member rotates the yoke and the first and second jaws within the capsule.

5. The device of claim 1, further comprising:
a handle which, during use of the device, remains outside a living body accessible to a user of the device, the handle including a first actuator operable to move the control member proximally and distally relative to the capsule and a second actuator to rotate the control member about a longitudinal axis of the capsule.

6. The device of claim 5, further comprising:
a flexible elongated member extending from a proximal end coupled to the handle to a distal end coupled to the capsule, the elongated member receiving the control member therein.

7. The device of claim 6, wherein the elongated member is sized to be slidably received within a working channel of an endoscope.

8. The device of claim 6, wherein the elongated member is coupled to the capsule via a bushing.

9. The device of claim 6, wherein the capsule is configured to rotate about the longitudinal axis of the capsule.

10. The device of claim 6, wherein the elongated member is formed as a flexible coil.

11. The device of claim 1, wherein an end effector including the first jaw, the second jaw, and the yoke has a length of less than 4 mm.

12. The device of claim 11, wherein the end effector has a length no more than 3.5 mm.

13. The device of claim 1, wherein the protrusions of the capsule are sized and shaped to meet the radially projecting portions of the yoke as the first and second jaws and the yoke move distally out of the distal end of the capsule.

* * * * *